(12) United States Patent
Marchi

(10) Patent No.: US 8,460,281 B2
(45) Date of Patent: Jun. 11, 2013

(54) LASER APPARATUS FOR HUMAN SKIN MEDICAL TREATMENT

(75) Inventor: Dante Marchi, Modena (IT)

(73) Assignee: Lasering S.r.l., Modena (IT)

( * ) Notice: Subject to any disclaimer, the term of this patent is extended or adjusted under 35 U.S.C. 154(b) by 661 days.

(21) Appl. No.: 12/448,994

(22) PCT Filed: Jan. 28, 2008

(86) PCT No.: PCT/EP2008/000654
§ 371 (c)(1),
(2), (4) Date: Mar. 3, 2010

(87) PCT Pub. No.: WO2008/092626
PCT Pub. Date: Aug. 7, 2008

(65) Prior Publication Data
US 2010/0174276 A1    Jul. 8, 2010

(30) Foreign Application Priority Data
Jan. 30, 2007  (IT) .............................. MO2007A0030

(51) Int. Cl.
*A61B 18/18* (2006.01)

(52) U.S. Cl.
USPC ............................................................ 606/9

(58) Field of Classification Search
USPC ...................................................... 606/15, 9, 3
See application file for complete search history.

(56) References Cited

U.S. PATENT DOCUMENTS

| 4,718,422 | A | | 1/1988 | Rosenberg |
| 5,995,265 | A | * | 11/1999 | Black et al. ................. 359/201.1 |
| 6,585,725 | B1 | * | 7/2003 | Mukai .............................. 606/10 |
| 2005/0049582 | A1 | * | 3/2005 | DeBenedictis et al. ........... 606/9 |
| 2006/0095096 | A1 | * | 5/2006 | DeBenedictis et al. ......... 607/88 |

FOREIGN PATENT DOCUMENTS

| GB | 2276014 | 9/1994 |
| WO | 96/22741 A | 8/1996 |
| WO | 98/24512 A | 6/1998 |

\* cited by examiner

*Primary Examiner* — Jessica Stultz
*Assistant Examiner* — Tuan Nguyen

(57) ABSTRACT

The invention relates to a field of systems for human skin medical treatments. The system consists in a biomedical apparatus (1) connected to a scanning device (5) by means of an articulated transmission system.

5 Claims, 3 Drawing Sheets

LASER APPARATUS FOR HUMAN SKIN MEDICAL TREATMENT

It is an object of the present invention a laser apparatus for human skin surface treatments.

The above mentioned laser apparatus enables to perform medical treatments such as resurfacing, skin rejuvenation, spot treatments and other human skin treatments by using an intermittent $CO_2$ laser beam generated by the biomedical apparatus and through an articulated transmission system conveyed to a scanning device, meant to direct said intermittent $CO_2$ laser beam towards the patient's skin according to a particular scanning algorithm described later.

It is known that a human skin surface treatment apparatus, which makes use of $CO_2$ laser beams, provides scanning systems which cover the skin area to be evenly treated using differently-sized spots or unevenly treated using spots with a diameter greater than 1 mm.

In both cases, the spots are positioned on said area according to criteria which in most cases cause:
  overheating of the skin area treated;
  flares and abrasions on said area;
  under treatment, pain around the treated skin area;
  the need for patients, who are particularly sensitive to pain, to take anaesthetic drugs which are not easily tolerated.

It is an aim of the present invention to overcome the above mentioned drawbacks.

Said aims are thoroughly achieved by means of the afore mentioned laser apparatus for the human skin surface treatment which is characterized by what stated in the appended claims.

Figure 1:
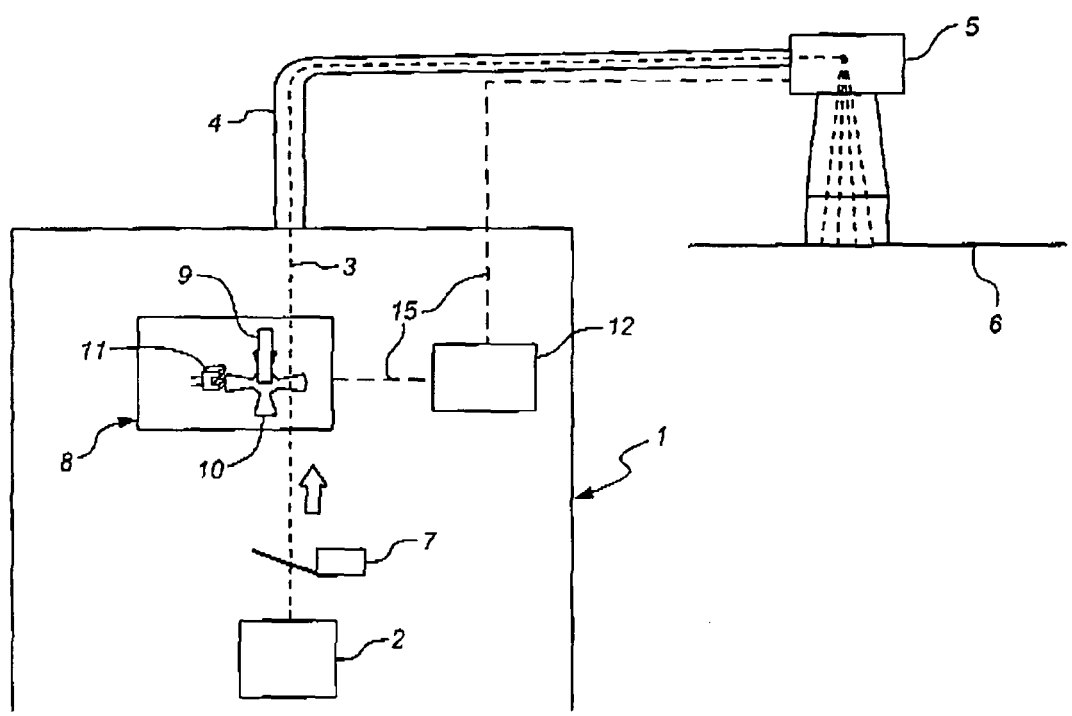

Features and drawbacks will be better understood from the following description of a preferred—but not exclusive—embodiment, to be considered by way of an example and not restrictive, as shown in the accompanying drawings, in which:

FIG. 1 is a schematic view of the functional components of the apparatus object of the present invention; while FIGS. 2, 3, 4 and 5 show the automatic positioning sequence of spots 14 within the skin area to be treated 13.

With reference to FIG. 1, element 1 is the biomedical apparatus consisting of a conventional $CO_2$ laser source 2, connected through an articulated transmission system 4, made up of either an articulated arm or an optical fibre system, to a scanning device 5, hand-operated, whose function is to radiate and direct the $CO_2$ laser beam 3 towards the patient's skin 6.

The biomedical apparatus 1 consists of a general safety shutter 7 which—when activated—allows the continuous $CO_2$ laser beam from the above mentioned laser source to go through; a blocking system 8 of said continuous $CO_2$ laser beam having an electric motor 9 which rotates a slotted disk 10 provided with alternate solid and empty sectors.

The above mentioned blocking system further provides an optical sensor 11 to detect the position of the solid and empty sectors of the slotted disk 10.

A control and guide device 12 for the mobile scanning device 5, connected to said element 5 and to the optical sensor 11 by means of wiring 15, is also provided.

Figure 2:
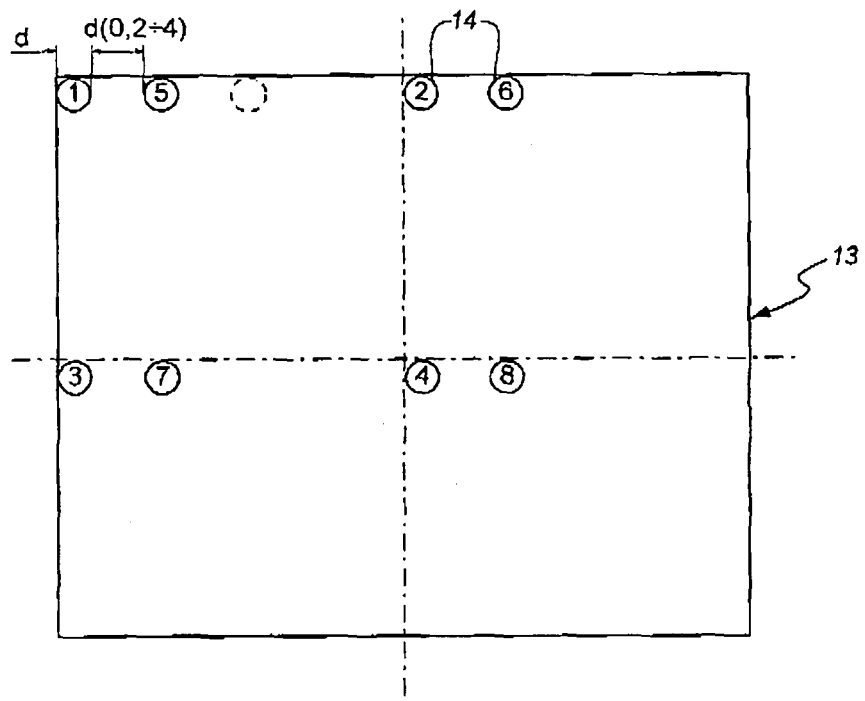
Figure 3:
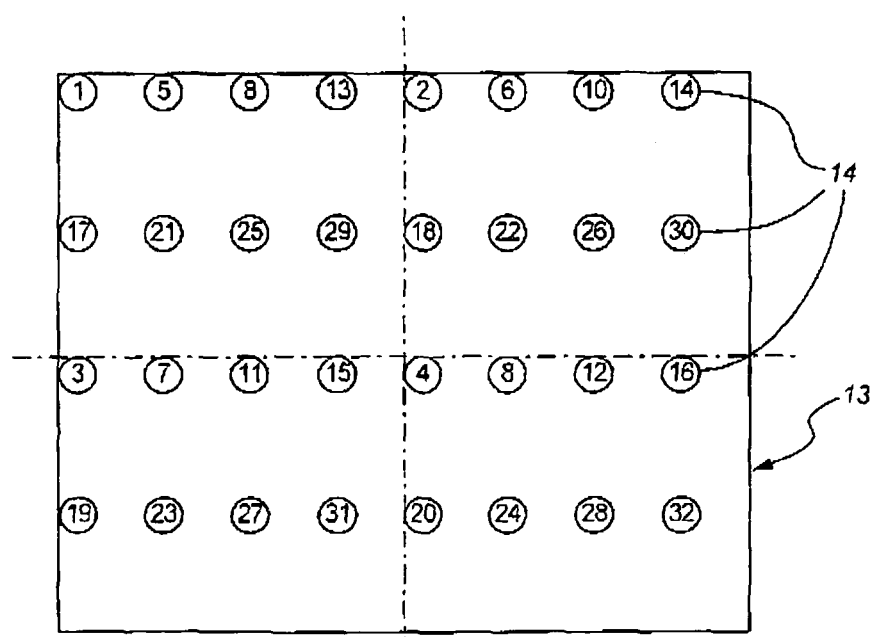
Figure 4:
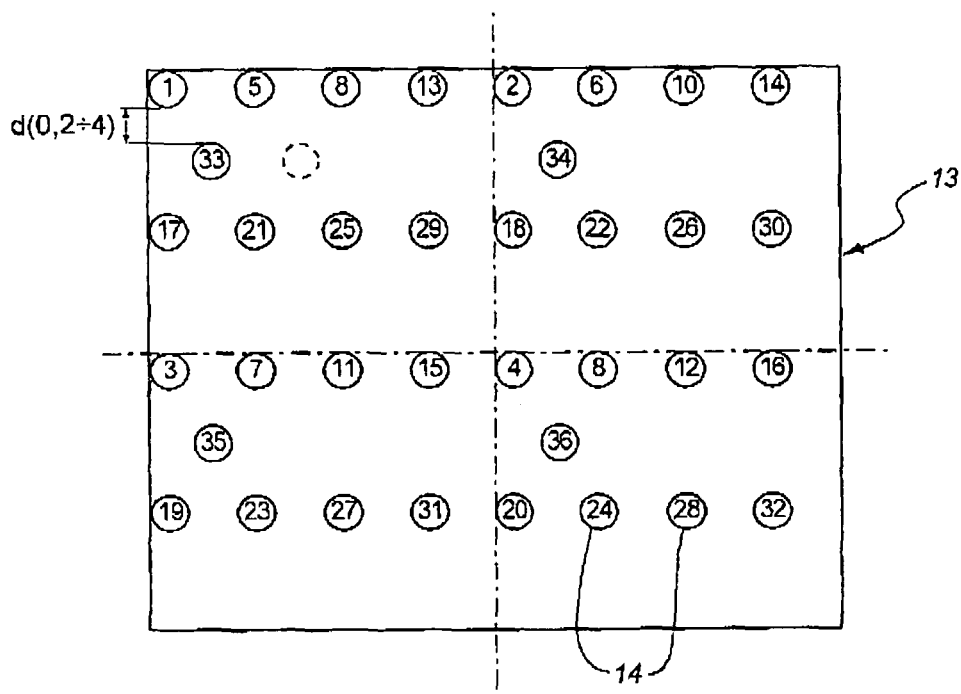

FIGS. 2, 3 and 4 schematically depict the positioning of spots 14 on the skin area to be treated 13 and the time sequence used by the scanning device 5 to position said spots within the aforementioned skin area, in the course of three successive treatment phases.

It should be noted that the term "spot" refers to the mark the $CO_2$ laser beam leaves on the patient's skin area hit by said beam.

Figure 5:
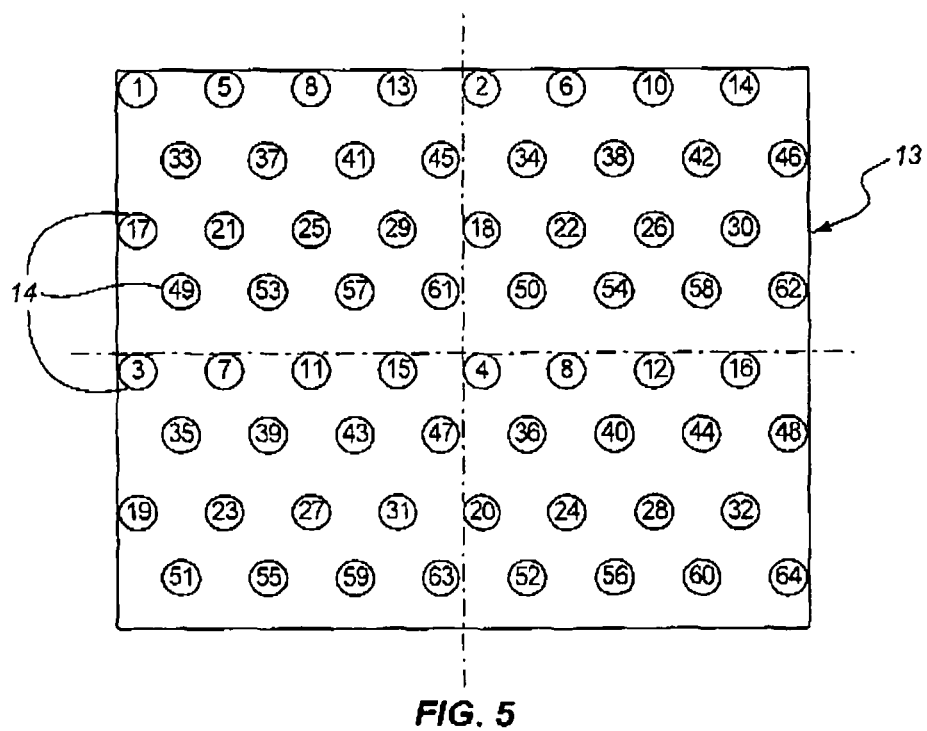

FIG. 5 shows the final pattern of the positioning of the spots inside the skin area to be treated.

It must be noted that during the automatic sequence positioning of the spots, the skin area to be treated 13 is assumed to be divided into four parts each having spots located exactly the same way, horizontally and vertically spaced apart at a distance ranging from 0.2 to 4 times the diameter of each spot, preferably 1.5 times.

Another relevant aspect of the present invention is that the final pattern, shown in FIG. 5, is obtained first by positioning the spots along alternate rows, as shown in FIG. 3, and then by filling the empty rows in a staggered ways to said alternate rows (see FIGS. 4 and 5). Obviously the number of spots inside the scanned area will depend on the diameter of the spots themselves and on the surface of the scanned skin.

The invention works as follow:

The medical treatment starts when the operator, after activating the laser source 2, opens the general safety shutter 7, enabling the biomedical apparatus 1 to supply $CO_2$ laser beams towards the patient's skin 6 by means of the scanning device 5.

Once the opening of the general safety shutter has been activated, the $CO_2$ laser beam passes through the blocking system, hitting the slotted disk rotating as shown in FIG. 1 and accordingly turning into an intermittent $CO_2$ laser beam whose life is proportional to the rotational speed of the slotted disk and to the number of slots in said disk.

Such intermittent laser beam will then go through an articulated transmission system consisting, for example, of an optical fibre or a multi-mirror articulated arm which will direct it towards the scanning device able to radiate said laser beam towards the patient's skin.

The optical sensor inside the blocking system has the function to detect the solid and empty sectors of the slotted disk and accordingly to verify the passage or the interrupting of the laser beam entering the blocking system (see FIG. 1).

By means of an electric signal, the optical sensor provides the detected position of the slotted disk for the control and guide device which, in turn, will synchronize the signal received to the movement of the motors, inside the scanning device, for directing the intermittent laser beam on the skin area to be treated. The control and guide device will ensure the moving of the motors to reach exactly the position along the coordinates where the next spot will hit the area to be treated exclusively in the space when the laser beam is blocked by a solid sector of the above mentioned slotted disk.

As the slotted disk 10 is continuously rotated by the electric motor 9, the passage of each solid sector of said disk is obviously followed by an empty one which will cause the $CO_2$ laser beam to go through the blocking system and to radiate towards the patient's skin and again the passage of another solid sector, during which the above stated motor swill position along the new coordinates of the next spot.

Clearly the skin exposure time to each $CO_2$ laser beam radiated from the scanning device 5 is a function of the rotational speed of the slotted disk 10 and the number of slots in said disk.

The above mentioned sequences of motor positioning and $CO_2$ laser beam emissions follow one another and continue till the end of each scan, that is till the positioning of the last spot inside each skin area to be treated.

During the scanning step, the control and guide device 12 determines the coordinates according to an algorithm as described from page 5, line 2 to page 6 line 1 which takes into account the scan size, the spot diameter and the thermal relaxing of every single skin area under treatment.

The invention claimed is:

1. Laser apparatus for human skin surface treatment comprising a biomedical apparatus (1) consisting of a conventional $CO_2$ laser source (2), connected through an articulated transmission system 4, made up of either an articulated arm or an optical fibre system, to a scanning device (5), whose function is to radiate and direct the $CO_2$ laser beam (3) towards the patient's skin (6), characterized in that comprises a. a general safety shutter (7) which - when activated - allows to a continuous $CO_2$ laser beam (3) from said laser source (2) to go through, b. a blocking system (8) of said continuous $CO_2$ laser beam (3) provided with a plurality of slots, of a slotted disk (10), alike and equally spaced apart and rotated by an electric motor (9) c. an optical sensor (11) inside the blocking system (8) having the function to detect the solid and empty sectors of slotted disk (10) and accordingly to verify the passage or the interrupting of the laser beam (3) entering the blocking system (8) d. a control and guide device (12) for the mobile scanning device (5), connected to said element (5) and to the optical sensor (11), once the opening of the general safety shutter has been activated, the $CO_2$ laser beam (3) passes through the blocking system (3), hitting the slotted disk rotating and turning into an intermittent $CO_2$ laser beam whose life is proportional to the rotational speed of the slotted disk (10) and to the number of slots in said disk; said intermittent laser beam will then go through an optical fibre or a multi-mirror articulated arm which will direct it towards the scanning device able to radiate said laser beam towards the patient's skin (6); by means of an electric signal, the optical sensor provides the detected position of the slotted disk for the control and guide device which, in turn, will synchronize the signal received to the movement of the motors, inside the scanning device, for directing the intermittent laser beam on the skin area to be treated; the control and guide device will ensure the moving of the motors to reach exactly the position along the coordinates here the next spot will hit the area to be treated exclusively in the space when the laser beam is blocked by a solid sector of the above mentioned slotted disk.

2. Apparatus according to claim 1, characterized in that the scanning device (5) provides the radiation of $CO_2$ laser beams (3) onto the skin area to be treated (13) according to a algorithm which takes into account the size of said area, the spot diameter and the thermal relaxing of every single skin area under treatment.

3. The apparatus according to claim 2, characterized in that, for each scan, the skin area to be treated (13) is assumed to be divided into four parts, spots (14) are equally located in each part with a distance to each other, both vertically and horizontally, ranging from 0,2 to 0,4 times the spot diameter.

4. The apparatus according to claims 3 characterized in that the positioning of spots (14) inside each imaginary quadrant of the skin area to be treated (13) takes place first by positioning the spots along alternate rows and then by filling the empty rows in a staggered way to said alternate rows.

5. The apparatus according to claims 3 characterized in that the diameter of spots (14) is at least smaller than 1 mm.

\* \* \* \* \*